United States Patent

Krivosha

[11] Patent Number: 5,645,525
[45] Date of Patent: Jul. 8, 1997

[54] HEEL STABILIZING DEVICE AND METHOD FOR TREATING HEEL PAIN

[75] Inventor: Ronald S. Krivosha, Bellevue, Wash.

[73] Assignee: Brown Medical Industries, Hartley, Iowa

[21] Appl. No.: 505,378

[22] Filed: Jul. 21, 1995

[51] Int. Cl.⁶ .................................................. A61F 5/00
[52] U.S. Cl. .................................................... 602/62
[58] Field of Search ........................ 602/60, 62, 65, 602/66, 23, 27; 682/19; 36/89; 128/892, 893

[56] References Cited

U.S. PATENT DOCUMENTS

| Re. 15,466 | 9/1922 | Hamilton | 602/65 |
|---|---|---|---|
| 2,744,152 | 12/1956 | Alber | 36/71 |
| 2,830,585 | 4/1958 | Weiss . | |
| 3,810,318 | 5/1974 | Epstein | 36/2.5 |
| 4,085,745 | 4/1978 | Alenares | 602/66 X |
| 4,179,826 | 12/1979 | Davidson | 36/69 |
| 4,266,298 | 5/1981 | Graziano | 2/22 |
| 4,287,675 | 9/1981 | Norton et al. | 36/129 |
| 4,325,380 | 4/1982 | Malkin . | |
| 4,409,976 | 10/1983 | Pence | 602/65 |
| 4,724,627 | 2/1988 | Sisco | 36/119 |
| 4,730,610 | 3/1988 | Graebe . | |
| 4,993,409 | 2/1991 | Grim | 602/19 |
| 4,999,932 | 3/1991 | Grim | 36/88 |
| 5,277,695 | 1/1994 | Johnson, Jr. et al. | 602/65 X |

FOREIGN PATENT DOCUMENTS

| 2316014 | 3/1973 | Germany . |
|---|---|---|
| 333156 | 11/1958 | Switzerland . |

Primary Examiner—Richard J. Apley
Assistant Examiner—Kim M. Lee
Attorney, Agent, or Firm—Zarley, McKee, Thomte, Voorhees, & Sease

[57] ABSTRACT

A heel stabilizing device is comprised of an elastic sleeve adapted to fit over the foot and heel of a person. The sleeve includes a pair of pads disposed on opposite sides of the inside surface of the sleeve. When the sleeve is worn around the heel, the two pads are positioned on opposite sides of the calcaneus. The pads exert opposite and equal forces to the medial and lateral side of the calcaneus to stabilize the heel within a shoe and also to impede the displacement of the fat pad located beneath the calcaneus.

21 Claims, 1 Drawing Sheet

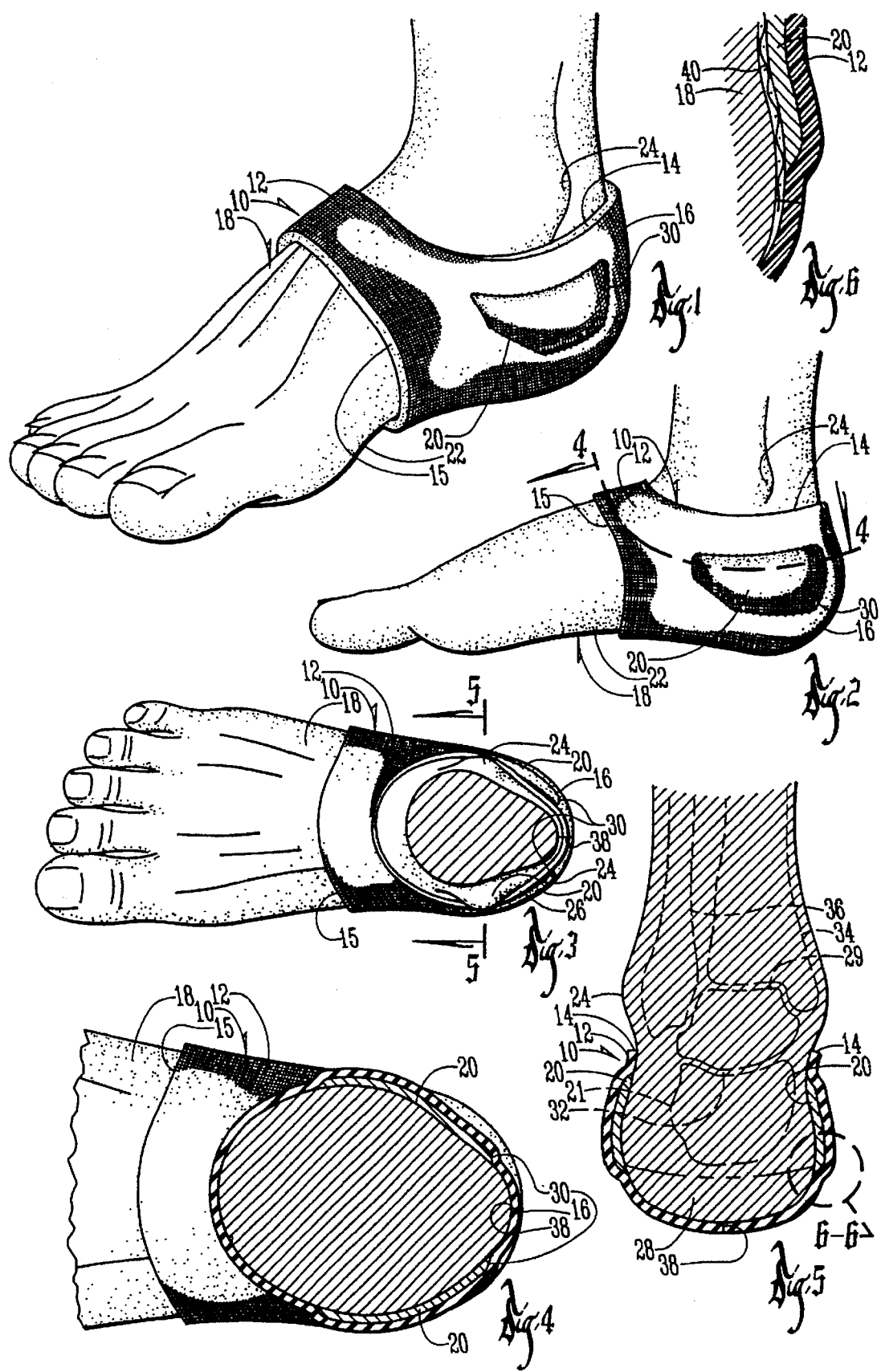

HEEL STABILIZING DEVICE AND METHOD FOR TREATING HEEL PAIN

BACKGROUND OF THE INVENTION

1. Field of the Invention

The present invention generally relates to devices and methods for stabilizing the heel and for the treatment of heel pain. More particularly, the present invention relates to devices and methods which apply pressure to the heel region of the foot for supporting and stabilizing the heel and treating heel pain while at the same time allowing a free range of motion of the ankle.

2. Problems in the Art

There are prior art devices which are used to treat ankle pain by immobilizing the ankle and the foot. Such devices include tape, elastic wrappings, lace-up braces, or slip-on braces with straps. Other prior art devices include high top shoes with supports and inflatable bladders covering the ankle bones to support the ankle.

Like ankle pain, heel pain is also a relatively common complaint. However, heel pain is medically and anatomically distinguishable from ankle pain rendering prior art ankle braces ineffective in treating heel pain without affecting the range of motion of the ankle. Therefore, a need can be seen for effective ways to treat heel pain without affecting the range of motion of the ankle.

The ethiology of heel pain includes (1) trauma, such as contusions; (2) bio-mechanical conditions such as Pes Plano Valgus and Equinus; (3) anatomical abnormalities such as heel spurs, narrow heels, and a decreased plantar fat pad; (4) inflammatory problems such as bursitis, tendonitis, plantar fascitis, calcaneoapophysitis; and (5) poorly fitted shoes.

Prior art methods to treat heel pain include ice therapy, limiting weight bearing, heel pads, heel cups, orthotic devices, surgical procedures, immobilization casting, and oral and injected anti-inflammatory medications.

Therefore, it can be seen that there is a need for an easy and effective device and method for treating heel pain.

FEATURES OF THE INVENTION

A general feature of the present invention is the provision of a device and method for stabilizing the heel of the foot.

A further feature of the present invention is the provision of a device and method for supporting and stabilizing the heel of the foot in order to treat heel pain.

A further feature of the present invention is the provision of a device and method for stabilizing the heel using an elastic sleeve adapted to fit around the heel of the foot.

A further feature of the present invention is the provision of a device and method for supporting the heel having a pair of pads which, when the device is worn, are positioned at the lateral and medial sides of the calcaneus (the heel bone).

A further feature of the present invention is the provision of a device and method for supporting the heel having a pair of pads formed on the interior surface of the device positioned at the lateral and medial sides of the calcaneus and below the talo calcaneal joint so that the heel is stabilized while the ankle is allowed to move freely.

A further feature of the present invention is the provision of a device and method for supporting the heel which will act to reduce the displacement of the fat pad from under the heel and thus cushion and protect the calcaneus while walking.

A further feature of the present invention is the provision of a device and method for supporting the heel that is adaptable to fit different sized feet, can be worn on either the left or right feet, and to be worn separately or with a variety of footwear.

A further feature of the present invention is the provision of a device and method for stabilizing the heel that adds to the stability affecting the heel counter of the shoe and helps hold the heel stable in the shoe via the stocking and the stabilizing pads at the level of the calcaneus.

A further feature of the present invention is the provision of a device and method for supporting the heel having a pair of pads made from fluid-filled bladders.

These as well as other features of the present invention will become apparent from the following specification and claims.

SUMMARY OF THE INVENTION

The heel stabilizing device and method for treating heel pain for the present invention is a device which stabilizes the heel of the foot while at the same time allows a free range of motion of the ankle. The device and method also prevents the displacement of the fat pad located beneath the calcaneus which helps to cushion the heel when walking. The device is preferably worn with a shoe to stabilize the position of the calcaneus within the shoe. The device is comprised of a sleeve which can be inserted over the toes and heel of the foot so as to encircle the heel. A pair of pads are disposed on the sleeve on opposite sides. The pads are positioned on the sleeve such that when the sleeve is worn around the heel the pads are disposed proximate the medial and lateral sides of the calcaneus and below the talo calcaneal joint. The pads exert opposite and equal compressive forces to the calcaneus which stabilizes the heel and prevent displacement of the fat pad located beneath the calcaneus.

BRIEF DESCRIPTION OF THE DRAWINGS

FIG. 1 is an isometric view showing one embodiment of the present invention.

FIG. 2 is a reduced side view of the embodiment shown in FIG. 1 viewed from the medial side of the foot.

FIG. 3 is a top view of the embodiment shown in FIG. 2.

FIG. 4 is a sectional view taken along line 4—4 in FIG. 2.

FIG. 5 is a sectional view taken along line 5—5 in FIG. 3.

FIG. 6 is an enlarged view taken along line 6—6 in FIG. 5.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention.

FIG. 1 shows the preferred embodiment of the present invention. The heel stabilizing device 10, is comprised of a half stocking 12 having an open top 14 and an open forward end 15. The stocking is made of a stretchable material so as to fit snugly around the posterior, lateral, medial, and plantar aspects of the heel 16 of the foot 18. Device 10 includes a pad 20 on each side of the inside surface of the stocking 12 proximate the calcaneus 21 of the heel 16. As shown in FIG. 6, the pads 12 are disposed in a pocket formed by sewing a piece of material 40 to the sleeve 12. When the stocking 12 is positioned over the heel 16, it extends forward along the lateral and medial sides of the foot 18 to approximately the mid-point of the longitudinal arch 22 of the foot 18 (FIGS. 1 and 2). It is important to note that the top 14 of the stocking 12 terminates at the calcaneus 21 below the talo calcaneal joint 32 of the foot 18 and therefore does not reach the ankle 24 or the tibia 34 or fibula 36. Together, stocking 12 and pads 20 stabilize the position of the calcaneus 21 below the talo calcaneal joint 32.

Device 10 has mirror image left and right lateral portions, such that the device can be worn on either foot 18. The device 10 can also be used alone or in conjunction with any type of foot wear. Device 10 is also stretchable or elastic so that it may be used with different foot sizes.

Stocking 12 is preferably comprised of an elastic firm stitched material forming an elastic sleeve and is adapted to slide over the foot 18 of the user as shown in the figures to provide a tight fit around the heel 16. An example of acceptable material is neoprene. Preferably the material is cut and stitched so that the seam 38 extends centrally along the bottom of the foot and up the back of the heel.

Stabilization of the calcaneus 21 or the heel 16 can be used to treat heel pain and help correct various heel-related conditions. Stabilizing the calcaneus 21 reduces movement and irritation to the heel which leads to inflammatory problems. Also, by applying pressure on opposite sides of the calcaneus 21 below the talo calcaneal joint 32, the fat pad 28 under the calcaneus may be prevented from moving from its natural position under the calcaneus 21. This is intended to protect the heel bone from impact by absorbing some of the shock during the heel contact phase of gait. This in turn can relieve heel pain.

Pads 20 are preferably comprised of a pair of bladders filled with a gel-type material, although pads 20 could take on many forms. For example, pads 20 could be foam pads or bladders filled with a fluid. The bladders are preferably made of a urethane material. Pads 20 are spaced apart and disposed on opposite sides of the inside surface of the elastic sleeve 12 such that when device 10 is worn around heel 16, pads 20 are positioned on the lateral and medial sides of the heel bone (calcaneus) at an elevation on the foot 18 below the talo calcaneal joint 32 (the joint located between the talus 29 and the calcaneus 21) as shown in FIGS. 2 and 5. Pads 20 do not extend over the Achilles tendon or the posterior aspect of heel 16. As best shown in FIGS. 2 and 4, rear edges 30 of pads 20 terminate before reaching the Achilles tendon or the posterior aspect of heel 16. Pads 20 also do not extend to the talo calcaneal joint 32, and therefore do not interfere with the ankles which allows the ankles to have a free range of mobility.

In the preferred embodiment, pads 20 are shaped as shown in FIGS. 1 and 2 to provide optimum heel Stabilization and fat pad displacement. Pads 20 are designed to compress heel 16 by exerting pressure only on the lateral and medial aspects of the calcaneus 21 and not the posterior aspect of heel 16. Pads 20 may take on many shapes, the embodiment shown in the Figures is only one example.

Pads 20 exert equal and opposite compressive forces against the calcaneus 21 and thereby stabilize the calcaneus 21 when device 10 is worn, especially within a shoe. Note that no compressive force from pads 20 is applied to the ankle, talo calcaneal joint 32, or to the posterior aspects of heel 16.

Pads 20 are disposed at a sufficiently low position on device 10 such that they limit some displacement of fat pad 28 from the plantar (bottom) surface of the calcaneus 21 thus protecting the plantar surface of the calcaneus 21 at the contact point of gait (walking). This fat pad 28 on the plantar aspect of the calcaneus 21 acts as a cushioning protective layer which reduces impact on the plantar surface of the calcaneus 21 during the stance phase of gait (FIG. 5). By spacing pads 20 apart on opposite sides of the calcaneus 21, the individual wearing device 10 will have both heel stability and at the same time the ankle 24 will have free range of motion since device 10 does not make contact with the ankle 24. Rather, the device 10 surrounds the foot and heel below the ankle.

The advantages of using a heel stabilizer such as device 10 with two pads such as pads 20 which exert equal but opposite compressive forces to the lateral and medial aspects of the calcaneus 21 can best be understood by reviewing FIGS. 3–5. Pads 20 exert pressure on the lateral and medial sides of the calcaneus 21 which act to hold or stabilize the calcaneus 21 of the foot 18 within a shoe. By stabilizing the calcaneus 21 in this manner, irritation and inflammation of the calcaneus 21 and the adjacent tissues is reduced, which reduces heel pain. Also, as shown in FIG. 5, when pads 20 exert pressure laterally and medially to the calcaneus 21, they prevent displacement of the fat pad 28 by stabilizing the position of fat pad 28 on the plantar, lateral, and medial aspects of the calcaneus 21. This fat pad provides a layer of cushion to protect the calcaneus 21. The sleeve 12 also cushions the calcaneus 21 somewhat.

Device 10 may be used with or without a shoe to treat several foot conditions. Note that the device 10 can be used with any type of shoe and is interchangeable between shoes. First, device 10 may be used to reduce heel Valgus or Varus which may cause irritation of the calcaneus and related structures. Second, device 10 may be used to reduce formation of bursa and bone spurs. Third, device 10 may be used with small children with calcaneal apophysitis to stabilize and elevate the heel 16 to prevent and/or reduce inflammation of the growth plate located within the calcaneus. Also, the pads 20 or the entire device 10 may be cooled prior to wearing so as to reduce swelling or inflammation in the ankle.

In addition to these uses, device 10 may be used to improve the fit of a shoe for individuals having narrow heels. Many people must wear larger sized shoes because they have a wide forefoot. When they wear a larger sized shoe, their heel moves around in the shoe because the shoe is large enough to take pressure off of the front of their foot. The device 10 compensates for a narrow heel by reinforcing the counter of the shoe and therefore makes the shoe fit better by holding the foot in a stable position.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A device for stabilizing the heel of a foot comprising:
   an elastic sleeve adapted to fit around the foot and heel of a person the sleeve having a front toe opening and a top ankle opening, when in operative position on a person's foot the toe opening is located to position a border thereof along the longitudinal arch, the top ankle opening is located to position a border thereof to extend above the heel without making contact with the ankle so as not to effect the mobility of the ankle; and a first and second pad positioned on opposite sides of the sleeve adjacent the border of the top ankle opening proximate the medial and lateral sides of the calcaneus of the heel and below both the talo calcaneal joint and the ankle for applying pressure to the calcaneus.

2. The device of claim 1 wherein the first and second pads each comprise a fluid-filled bladder.

3. The device of claim 2 wherein the bladder is filled with a gel.

4. The device of claim 2 wherein the bladder is filled with air.

5. The device of claim 2 wherein the bladder is filled with a liquid.

6. The device of claim 1 wherein the pads are constructed of foam material.

7. The device of claim 1 wherein the sleeve has interior and exterior surfaces, and the first and second pads are disposed on the inside surface of the sleeve.

8. The device of claim 1 wherein the first and second pads exert opposite pressure to the heel proximate the medial and lateral aspects of the calcaneus for preventing displacement of the fat pad disposed underneath the calcaneus.

9. The device of claim 1 wherein the sleeve has mirror image left and right portions so as to be interchangeably worn on either the left or right foot of the person.

10. A device for stabilizing the heel of a foot within a shoe without effecting the mobility of the ankle and for impeding the displacement of the fat pad underneath the heel, comprising:

an elastic sleeve adapted to fit around the foot and heel of a person, the sleeve having a front toe opening and a top ankle opening, when in operative position on a person's foot the toe opening is located to position a border thereof along the longitudinal arch, the top ankle opening is located to position a border thereof to extend above the heel and below the ankle;

a pair of pads positioned on opposite sides of the elastic sleeve such that when the sleeve is positioned over the heel the pads will be adjacent the border of the top ankle opening proximate the medial and lateral sides of the calcaneus and below the talo calcaneal joint; and wherein said pads each exert a compressive force to the calcaneus stabilize the heel within the shoe and to impede the displacement of the fat pad underneath the heel.

11. The device of claim 10 wherein said pads are comprised of a compressible material.

12. The device of claim 10 wherein said pads are comprised of a pair of fluid-filled bladders.

13. The device of claim 12 wherein said bladders are filled with air.

14. The device of claim 12 wherein said bladders are filled with a liquid.

15. The device of claim 12 wherein said bladders are filled with a gel.

16. A method for selectively stabilizing a person's heel below the talo calcaneal joint without effecting the range of motion of the ankle joint, comprising the steps of:

placing an elastic sleeve having a front toe opening and a top ankle opening around the foot and heel of a person and below the ankle such that the toe opening is positioned along the longitudinal arch and the top ankle opening is positioned to extend above the heel and below the ankle; and positioning first and second pads adjacent a border of the top ankle opening proximate the medial and lateral sides of the calcaneus below the talo calcaneal joint such that the pads exert pressure on the medial and lateral sides of the heel to stabilized the heel without exerting pressure on the ankle joint.

17. The method of claim 16 further comprising the step of inserting said foot and elastic sleeve into a shoe.

18. The method of claim 16 further comprising the step of cooling said first and second pads before inserting said sleeve over the foot and heel.

19. The device of claim 1 wherein the first and second pads are positioned entirely below the talo calcaneal joint.

20. The device of claim 10 wherein the pair of pads are positioned entirely below the talo calcaneal joint.

21. The device of claim 1 wherein the first and second pads each terminate before reaching the posterior aspect of heel so that the pads do not extend over or come into contact with the Achilles tendon.

* * * * *